US010571435B2

(12) United States Patent
Gilbert

(10) Patent No.: US 10,571,435 B2
(45) Date of Patent: Feb. 25, 2020

(54) SYSTEMS AND METHODS FOR DIGITAL CONTROL OF ULTRASONIC DEVICES

(71) Applicant: COVIDIEN LP, Mansfield, MA (US)

(72) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 183 days.

(21) Appl. No.: 15/617,151

(22) Filed: Jun. 8, 2017

(65) Prior Publication Data

US 2018/0356367 A1    Dec. 13, 2018

(51) Int. Cl.
*A61B 17/32* (2006.01)
*G01N 29/36* (2006.01)
(Continued)

(52) U.S. Cl.
CPC .............. *G01N 29/14* (2013.01); *A61B 8/14* (2013.01); *A61B 8/4444* (2013.01); *A61B 17/32* (2013.01);
(Continued)

(58) Field of Classification Search
CPC .......... G01N 29/14; G01N 29/36; A61B 8/14; A61B 8/4444; A61B 117/32; A61B 17/320068; A61B 17/320092; A61B 2017/0003; A61B 2017/00017; A61B 2017/00075; A61B 2017/00106; G01H 1/003; G01M 3/24
(Continued)

(56) References Cited

U.S. PATENT DOCUMENTS 1,813,902 A    7/1931   Bovie
2,874,470 A    2/1959   Richards
(Continued)

FOREIGN PATENT DOCUMENTS

EP    0 705 570 A1    4/1996
EP      908148 A1     4/1999
(Continued)

OTHER PUBLICATIONS

Lessons in Electric Circuits, vol. 1—Direct Current (DC), chapter 13—Capacitor, pp. 2-8, by Tony R. Kuphaldt (Year: 2006).*
(Continued)

*Primary Examiner* — Suman K Nath

(57) ABSTRACT

An ultrasonic transducer and generator assembly and method for controlling the assembly are disclosed. The method includes sensing a current signal and a voltage signal at the transducer, differentiating the voltage signal, multiplying the differentiated voltage signal by a bulk capacitance value to determine a bulk capacitance current signal, determining the difference between the current signal and the bulk capacitance current signal to determine a motional current signal corresponding to mechanical motion of the transducer, determining an updated bulk capacitance value based on the determined motional current signal and the bulk capacitance current signal, generating a transducer signal based on the motional current signal, and driving the transducer with the transducer signal. The method may further include filtering the difference between the current signal and the bulk capacitance current signal using a band-pass filter. The updated bulk capacitance may be determined using a least mean squares adaptive filter.

20 Claims, 9 Drawing Sheets

(51) Int. Cl.
*A61B 17/00* (2006.01)
*G01N 29/14* (2006.01)
*A61B 8/14* (2006.01)
*A61B 8/00* (2006.01)
*G01H 1/00* (2006.01)
*G01M 3/24* (2006.01)

(52) U.S. Cl.
CPC ............ *A61B 17/320068* (2013.01); *A61B 17/320092* (2013.01); *G01H 1/003* (2013.01); *G01M 3/24* (2013.01); *G01N 29/36* (2013.01); *A61B 2017/0003* (2013.01); *A61B 2017/00017* (2013.01); *A61B 2017/00075* (2013.01); *A61B 2017/00106* (2013.01)

(58) Field of Classification Search
USPC .......................................... 73/632; 702/64
See application file for complete search history.

(56) References Cited

U.S. PATENT DOCUMENTS

| | | |
|---|---|---|
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,175,242 A | 11/1979 | Kleinschmidt |
| 4,193,818 A | 3/1980 | Young et al. |
| 4,223,676 A | 9/1980 | Wuchinich et al. |
| 4,275,363 A | 6/1981 | Mishiro et al. |
| 4,277,758 A | 7/1981 | Mishiro |
| 4,300,083 A | 11/1981 | Heiges |
| 4,302,728 A | 11/1981 | Nakamura |
| 4,493,694 A | 1/1985 | Wuchinich |
| 4,504,264 A | 3/1985 | Kelman |
| 4,587,958 A | 5/1986 | Noguchi et al. |
| 4,641,053 A | 2/1987 | Takeda |
| 4,689,514 A | 8/1987 | Kondoh et al. |
| 4,724,401 A | 2/1988 | Hogge, Jr. et al. |
| 4,747,820 A | 5/1988 | Hornlein et al. |
| 4,754,186 A | 6/1988 | Choperena et al. |
| 4,879,528 A | 11/1989 | Gotanda |
| 4,886,060 A | 12/1989 | Wiksell |
| 4,898,574 A | 2/1990 | Uchiyama et al. |
| 4,965,532 A | 10/1990 | Sakurai |
| 4,979,952 A | 12/1990 | Kubota et al. |
| 5,026,387 A | 6/1991 | Thomas |
| 5,139,509 A | 8/1992 | Fischer et al. |
| 5,151,085 A | 9/1992 | Sakurai et al. |
| 5,162,044 A | 11/1992 | Gahn et al. |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,421,829 A | 6/1995 | Olichney et al. |
| 5,451,220 A | 9/1995 | Ciervo |
| 5,490,860 A | 2/1996 | Middle et al. |
| 5,565,520 A | 10/1996 | Fock et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,792,138 A | 8/1998 | Shipp |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,016,052 A | 1/2000 | Vaughn |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,100,654 A | 8/2000 | Izukawa et al. |
| 6,162,194 A | 12/2000 | Shipp |
| 6,183,426 B1 | 2/2001 | Akisada et al. |
| 6,254,623 B1 | 7/2001 | Haibel, Jr. et al. |
| 6,257,241 B1 | 7/2001 | Wampler |
| 6,261,249 B1 | 7/2001 | Talish et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,569,109 B2 | 5/2003 | Sakurai et al. |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,630,768 B2 | 10/2003 | Yamashiro et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,761,690 B2 | 7/2004 | Sakurai et al. |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |

(56) References Cited

U.S. PATENT DOCUMENTS

| | | |
|---|---|---|
| 7,218,030 B2 | 5/2007 | Kasuga et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,345,401 B2 | 3/2008 | Schief |
| 7,564,163 B2 | 7/2009 | Onoda et al. |
| 7,821,143 B2 | 10/2010 | Wiener |
| 8,333,778 B2 | 12/2012 | Smith et al. |
| 8,659,208 B1 | 2/2014 | Rose et al. |
| 9,782,180 B2 | 10/2017 | Smith et al. |
| 2002/0091339 A1 | 7/2002 | Horzewski et al. |
| 2002/0138090 A1 | 9/2002 | Jewett |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0162509 A1 | 8/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0209620 A1 | 9/2005 | Du et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0239028 A1 | 10/2007 | Houser et al. |
| 2007/0239101 A1 | 10/2007 | Kellogg |
| 2008/0033248 A1 | 2/2008 | Akagi |
| 2008/0051693 A1 | 2/2008 | Babaev |
| 2008/0245841 A1 | 10/2008 | Smith et al. |
| 2009/0143805 A1 | 6/2009 | Palmer et al. |
| 2009/0223033 A1 | 9/2009 | Houser |
| 2011/0087256 A1* | 4/2011 | Wiener ............... A61B 18/1206 606/169 |
| 2012/0127009 A1* | 5/2012 | Pagnanelli ............ H03M 3/468 341/143 |
| 2013/0289591 A1* | 10/2013 | Boudreaux .... A61B 17/320068 606/169 |
| 2016/0089533 A1* | 3/2016 | Turner ........... A61B 17/320092 606/34 |

FOREIGN PATENT DOCUMENTS

| | | |
|---|---|---|
| EP | 1 594 209 A1 | 11/2005 |
| EP | 1707131 A1 | 10/2006 |
| EP | 2 200 145 A1 | 6/2010 |
| WO | 2006/087885 A1 | 8/2006 |
| WO | 2006/119376 A2 | 11/2006 |
| WO | 2007/047380 A2 | 4/2007 |
| WO | 2013154923 A2 | 10/2013 |
| WO | 2013158537 A2 | 10/2013 |

OTHER PUBLICATIONS

Extended European Search Report issued in corresponding application No. 18176466.3 dated Oct. 1, 2018, 8 pages.

* cited by examiner

SYSTEMS AND METHODS FOR DIGITAL CONTROL OF ULTRASONIC DEVICES

BACKGROUND

1. Technical Field

The present disclosure relates generally to ultrasonic devices and, more particularly, relates to digital control of ultrasonic devices.

2. Background of the Related Art

Ultrasonic surgical instruments are used in the treatment of many medical conditions, such as the removal of tissue and the cauterization and sealing of vessels. Cutting instruments that utilize ultrasonic waves generate vibrations with an ultrasonic transducer and transmit them along a longitudinal axis of a cutting blade. By transmitting an ultrasonic wave along the length of the blade, high-speed longitudinal mechanical movement is produced at the end of the blade. These surgical instruments are advantageous because the mechanical vibrations transmitted to the end of the blade are effective at cutting organic tissue and simultaneously coagulate the tissue using the heat energy produced by the mechanical vibrations. Such surgical instruments are well suited for use in minimally invasive procedures, such as endoscopic or laparoscopic procedures, where the blade is passed through a trocar to reach the surgical site.

For each kind of cutting blade, there are one or more periodic drive signals that cause the transducer to mechanically vibrate at the resonance frequency to provide an ultrasonic wave along the length of the blade. Resonance results in optimal movement of the blade tip and thus optimal performance during surgical procedures. However, producing an effective cutting-blade drive signal is not trivial. For instance, the frequency, current, and voltage applied to the cutting tool must all be controlled dynamically, as these parameters change with the varying load placed on the blade during use of the tool.

SUMMARY

One aspect of the present disclosure features a method for controlling a transducer and generator assembly. The method includes sensing a current signal and a voltage signal at a transducer, differentiating the voltage signal, multiplying the differentiated voltage signal by a bulk capacitance value to determine a bulk capacitance current signal, determining the difference between the current signal and the bulk capacitance current signal to determine a motional current signal corresponding to mechanical motion of the transducer, determining an updated bulk capacitance value based on the determined motional current signal and the bulk capacitance current signal, generating a transducer signal based on the motional current signal, and driving the transducer with the transducer signal.

In another aspect, the method further includes amplifying the current signal or the voltage signal, thereby increasing a magnitude of the transducer signal. In a further aspect, the method includes determining a phase of the motional current signal, and varying the frequency of the transducer signal based on the phase of the motional current signal. In another aspect, the method includes determining an initial value of the bulk capacitance prior to providing the transducer signal to the transducer.

In yet another aspect, the method includes determining the updated bulk capacitance using a least mean squares adaptive filter. In another aspect, the method includes determining the updated bulk capacitance using a normalized least mean squares adaptive filter.

In another aspect, filtering the voltage signal is done using a zero-delay median filter, and differentiating the voltage signal using a zero-delay differentiator. In another aspect, the method includes sampling the voltage signal to obtain voltage data, and wherein differentiating the voltage signal includes determining a rate of change of the voltage signal based on the sampled voltage data. In yet another aspect, filtering the voltage signal, sampling the voltage signal, and determining the rate of change of the voltage signal do not cause time-delay or phase distortion greater than a predetermined threshold.

In another aspect, the method includes determining a frequency of the transducer signal based at least in part on a phase of the motional current signal. In another aspect the method includes determining a root mean square voltage of the voltage signal, determining a root mean square current of the current signal, and determining an average power and an apparent power based on the root mean square voltage and the root mean square current.

In another aspect, the method includes generating a test signal, transmitting the test signal to the transducer, sensing a response, and determining the initial value of the bulk capacitance based on the sensed response. In a further aspect, the method includes filtering the difference between the current signal and the bulk capacitance current signal using a band-pass filter to obtain the motional current signal. In yet another aspect, the method includes differentiating the voltage data using a two-point difference method, and filtering the differentiated voltage data using a low-pass filter.

In another aspect, the low-pass filter is a Hann moving average filter. In a further aspect, the method includes differentiating the voltage data using a three-point central difference method. The method of claim 17, further comprising filtering the differentiated voltage data using a low-pass filter. In another aspect, the low-pass filter is a Hann moving average filter.

An aspect of the present disclosure is directed towards a transducer and generator assembly. The transducer and generator includes a current sensor for sensing a current signal at the transducer, a voltage sensor for sensing a voltage signal at the transducer, an analog-to-digital converter ("ADC") coupled to the current sensor and the voltage sensor for sampling the current signal and the voltage signal to obtain current signal data and voltage signal data. The transducer and generator further include a hardware processor configured to differentiate the voltage signal data to obtain differentiated voltage signal data, multiplying the differentiated voltage signal data by a bulk capacitance value to obtain bulk capacitance current signal data; determine the difference between the current signal data and the bulk capacitance current signal data to obtain motional current signal data corresponding to mechanical motion of the transducer, update the bulk capacitance value based on the determined motional current signal and the bulk capacitance current signal data. The transducer and generator also include a transducer signal generator circuit configured to generate a transducer signal based on the motional current signal data and to providing the transducer signal to the transducer.

BRIEF DESCRIPTION OF THE DRAWINGS

Various embodiments of the subject instrument are described in the present disclosure with reference to the drawings wherein.

DETAILED DESCRIPTION

Figure 1:
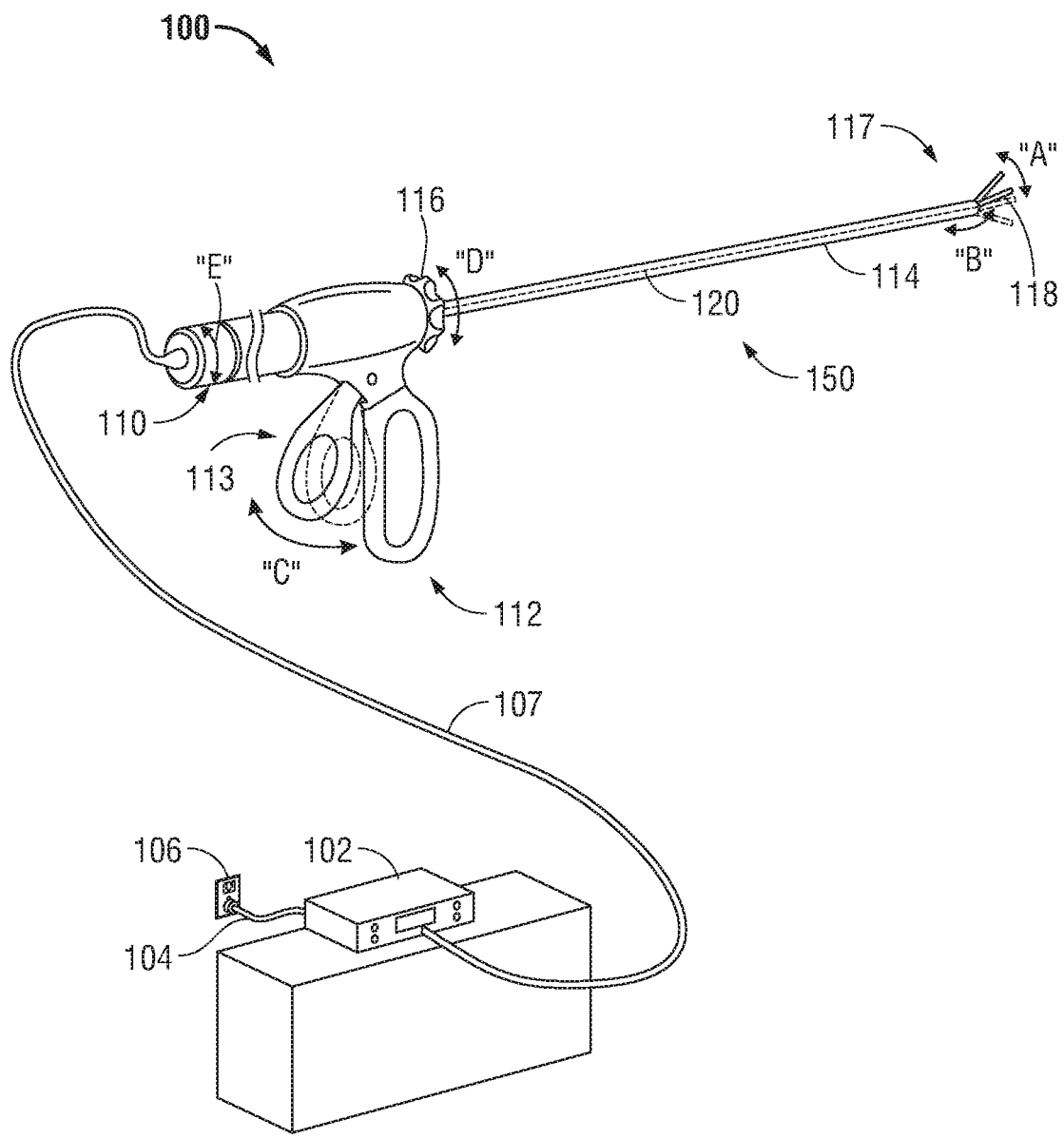
FIG. 1 is a perspective view of an ultrasonic surgical system illustrating components of the ultrasonic surgical system including an ultrasonic generator, in accordance with one illustrative embodiment of the present disclosure.

Particular embodiments of the present disclosure are described below with reference to the accompanying drawings. In the following description, well-known functions or constructions are not described in detail.

The disclosed embodiments are merely exemplary of the disclosure, which can be embodied in various forms. Therefore, specific structural and functional details are not to be interpreted as limiting, but merely as a basis for the claims and as a representative basis for teaching one skilled in the art to variously employ the present disclosure in any appropriately detailed structure. Further, the terms and phrases used herein are not intended to be limiting, but are intended to provide an understandable description of the disclosure.

The terminology used in this disclosure is for the purpose of describing particular embodiments and is not intended to be limiting. The terms "a" or "an", as used in this disclosure, are defined as one or more than one. The term "plurality," as used in this disclosure, is defined as two or more than two. The term "another," as used in this disclosure, is defined as at least a second or more. The terms "including" and/or "having," as used in this disclosure, are defined as comprising (i.e., open language). The term "coupled," as used in this disclosure, is defined as connected, although not necessarily directly, and not necessarily mechanically.

Relational terms such as first and second, top and bottom, and the like may be used to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used in this disclosure, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this disclosure, the term "longitudinal" should be understood to mean in a direction corresponding to an elongated direction of the object being described. As used in this disclosure, the terms "distal" and "proximal" are considered from the vantage of the user or surgeon; thus, the distal portion of a surgical instrument is that portion farthest away from the surgeon when in use, and the proximal portion is that portion generally closest to the user.

It will be appreciated that embodiments of this disclosure may be comprised of one or more conventional processors and memory having stored thereon program instructions that control the one or more processors to implement, in conjunction with certain other circuits and elements, some, most, or all of the functions of the ultrasonic surgical system described in this disclosure. The other circuits may include, but are not limited to, signal drivers, clock circuits, power source circuits, and user input and output elements. Alternatively, some or all functions of the ultrasonic surgical system could be implemented by a state machine, in one or more application specific integrated circuits (ASICs), in which each function or some combination of certain of the functions are implemented as custom logic, or in a field-programmable gate array (FPGA) enabling the use of updateable custom logic either by the manufacturer or the user. In embodiments, any combination of state machines, ASICs, and FPGAs could also be used.

The terms "program," "software application," and the like as used herein, are a sequence of instructions designed for execution on a computer system. A "program," "computer program," or "software application" may include a subroutine, a function, a procedure, an object method, an object implementation, an executable application, an applet, a servlet, source code, object code, a shared library/dynamic load library and/or other sequence of instructions designed for execution on a computer system.

FIG. 1 shows a diagram illustrating an ultrasonic surgical system 100, which generally includes ultrasonic generator 102 and an ultrasonic surgical instrument 150 for applying ultrasonic energy to tissue via an end effector 117. Ultrasonic surgical instrument 150 includes transducer 110, stationary hand-piece 112, moveable hand-piece 113, waveguide 114 acoustically coupled to transducer 110 (waveguide 114 is illustrated by a dashed line), rotating actuator 116, and cannula 120 housing waveguide 114. Waveguide 114 connects to a dissector probe 118 at a distal portion of waveguide 114. Transducer 110, waveguide 114, and dissector probe 118 form an oscillating structure that are generally configured to resonate at the same frequency. A clamping mechanism referred to as an "end effector" 117, exposes and enables dissector probe 118 of waveguide 114 to make contact with tissue. In embodiments, end effector 117 is a pivoting arm that acts to grasp or clamp tissue between the pivoting arm and dissector probe 118 along arrow "A." The clamping and grasping motion by end effector 117, along arrow "A," is effected by movement of moveable hand-piece 113 along arrow "B." In further embodiments, end effector 117 may be rotated or twisted along arrow "B" via rotating actuator 116, which is rotated along arrow "D." In other embodiments, end effector 117 is not present. Furthermore, the proximal portion of ultrasonic surgical instrument 150 is rotatable along arrow "E" thereby allowing transducer 110 to remain in contact with supply cord 104 as supply cord 107 is twisted or rotated during use of ultrasonic surgical instrument 150.

As shown in FIG. 1, ultrasonic surgical instrument 150 is tethered to ultrasonic generator 102 via supply cord 107. Because a relatively high voltage (e.g., 100 V or more) is required to drive a piezoelectric transducer 110, one commonly used power source is an electric mains (e.g., a wall outlet) of, typically, up to 15 A, 120 VAC. As illustrated in FIG. 1, ultrasonic generator 102 with electrical cord 104 to be plugged into electrical mains 106 is connected via supply cord 107 to ultrasonic surgical instrument 150.

Transducer 110 is an electromechanical device that converts electrical signals to physical or mechanical movement. One example of such an electromechanical device is a stack of piezoelectric crystals. In the present disclosure, the drive signal or driving wave (e.g., a sine wave) is input to the transducer 110, which then imparts mechanical movement to waveguide 114. As will be shown, this mechanical movement sets up a resonating wave on waveguide 114, resulting in motion at the end of waveguide 114.

In an embodiment where transducer 110 is formed of a stack of piezoelectric crystals, each piezoelectric crystal is separated from an adjacent piezoelectric crystal by an insulator. The piezoelectric crystals change their longitudinal dimension when a sinusoidal voltage is applied to all the piezoelectric crystals such that the stack expands and contracts as a unit. These expansions and contractions are at the frequency of the drive signal produced by the driving circuit 308. The mechanical movement of transducer 110 induces a sinusoidal wave along the length of the waveguide 114, thereby longitudinally moving dissector probe 118. Dissector probe 118 tip is ideally at an "anti-node," as it is a moving point of the sine wave. The resulting movement of the waveguide 114 produces a "sawing" movement in dissector probe 118 at the end of waveguide 114 providing a cutting motion that is able to slice through many materials, such as tissue and bone.

In certain embodiments, transducer 110 may additionally move in a different plane, thereby creating a torsional or twisting motion of dissector probe 118 rather than only a sawing motion. Waveguide 114 also generates frictional heat which is conducted within the tissue that dissector probe 118 contacts. This frictional heat is sufficient to cauterize blood vessels within the tissue being cut.

If the drive signal applied to transducer 110 and traveling along waveguide 114 is not at the resonant frequency for ultrasonic surgical instrument 150, the last anti-node may not appear at the tip of dissector probe 118 of waveguide 114. In such a case, the dissector probe 118 may move transverse to the longitudinal axis of waveguide 114. While off-resonant motion of dissector probe 118 is generally not desirable, in certain applications such off resonance motion may be desirable for certain periods of time to achieve certain surgical outcomes. Resonance is maintained by a digital signal processor, such as the digital signal processor shown in FIG. 3, which creates a closed loop between the output of ultrasonic generator 102 and the input of transducer 110. Resonance of transducer 110 is maintained by monitoring and adjusting current and voltage applied to transducer 110.

Ultrasonic generator 102 produces a high-voltage self-oscillating signal. Ultrasonic generator 102 contains signal-smoothing components that, in turn, produce a drive signal that is fed to transducer 110. The drive signal input to transducer 110 causes the mechanical portion of transducer 110 to move back and forth at a magnitude and frequency that achieves resonance along waveguide 114. For optimal resonance and longevity of the resonating instrument and its components, the drive signal applied to transducer 110 should be as smooth a sine wave as can practically be achieved. For this reason, ultrasonic generator 102, transducer 110, and waveguide 114 are selected to work in conjunction with one another.

Figure 2:
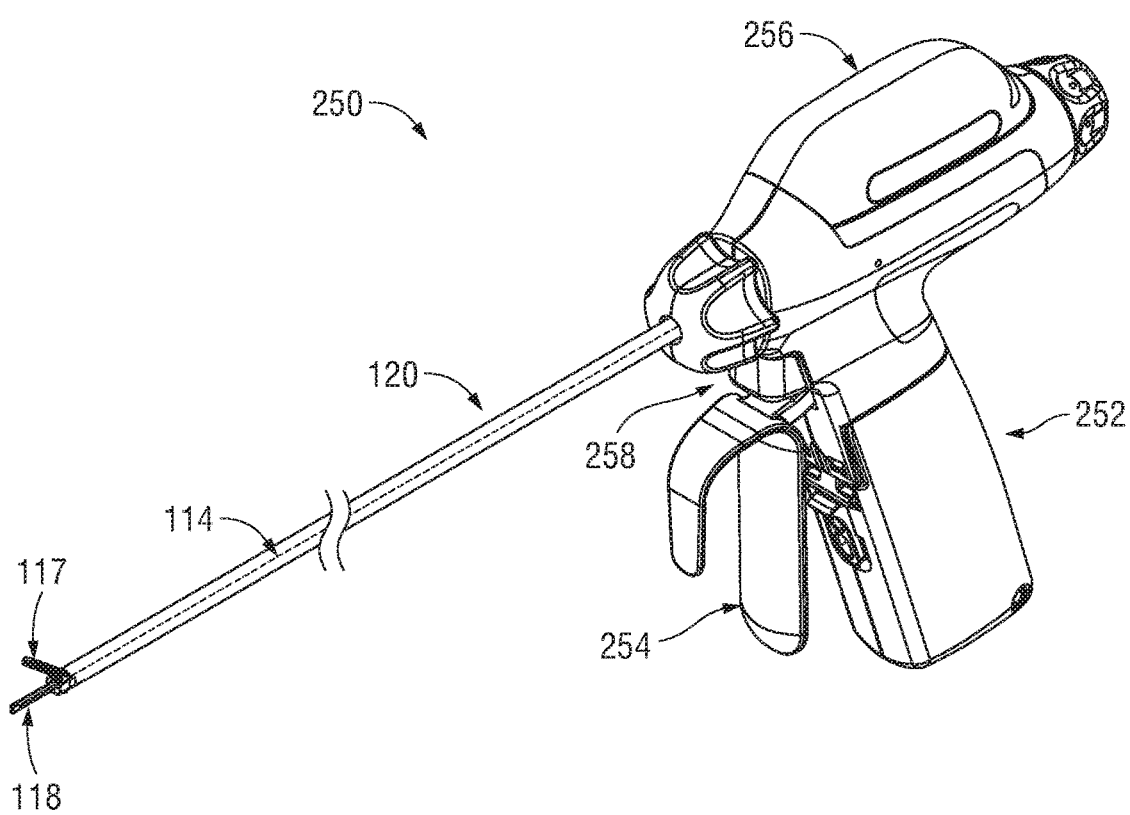
FIG. 2 is a perspective view of a portable ultrasonic surgical system incorporating an ultrasonic generator and a rechargeable battery, in accordance with another illustrative embodiment of the present disclosure.

FIG. 2 is a perspective view of a battery-operated hand-held ultrasonic surgical device 250 according to other embodiments of the present disclosure. As with the embodiment shown in FIG. 1, the distal portion of ultrasonic surgical instrument 250 includes an end effector 117 which incorporates dissector probe 118. End effector 117 and dissector probe 118 are disposed at the distal portion of cannula 120, which encloses waveguide 114. Waveguide 114 connects to dissector probe 118 so that acoustic waves propagate from waveguide 114 to the dissector probe 118.

Power for ultrasonic surgical device 250 is provided by battery 252. In the example depicted in FIG. 2, battery 252 is formed as an integral component of the ultrasonic surgical device 250. Battery 252, when connected to the rest of ultrasonic surgical instrument 250, forms the handle. In an alternative arrangement, battery 252 may be removably housed within a compartment of the handle. A variety of alternative arrangements for battery 252 and its incorporation into ultrasonic surgical instrument 250 are described in commonly-assigned U.S. Pat. No. 8,403,949, titled "Cordless hand-held ultrasonic cautery cutting device," filed Nov. 12, 2008, to Matthew A. Palmer, which is incorporated by reference herein.

Battery 252 is formed of one or more rechargeable cells (not shown). For example, the battery may include four cells, each of which has a nominal voltage of approximately 3.7 V/cell, connected in series, resulting in a nominal battery voltage of approximately 15 V. Battery 252 may be a so-called "Smart Battery" for which many functions, including how it is charged and discharged, are controlled by one or more microcontrollers connected to the cells within the housing of battery 252, as described in the Smart Battery Data Specification, Revision 1.1, which was first published on Dec. 11, 1998, by the Smart Battery System Implementers Forum (SBS-IF).

Figure 3:
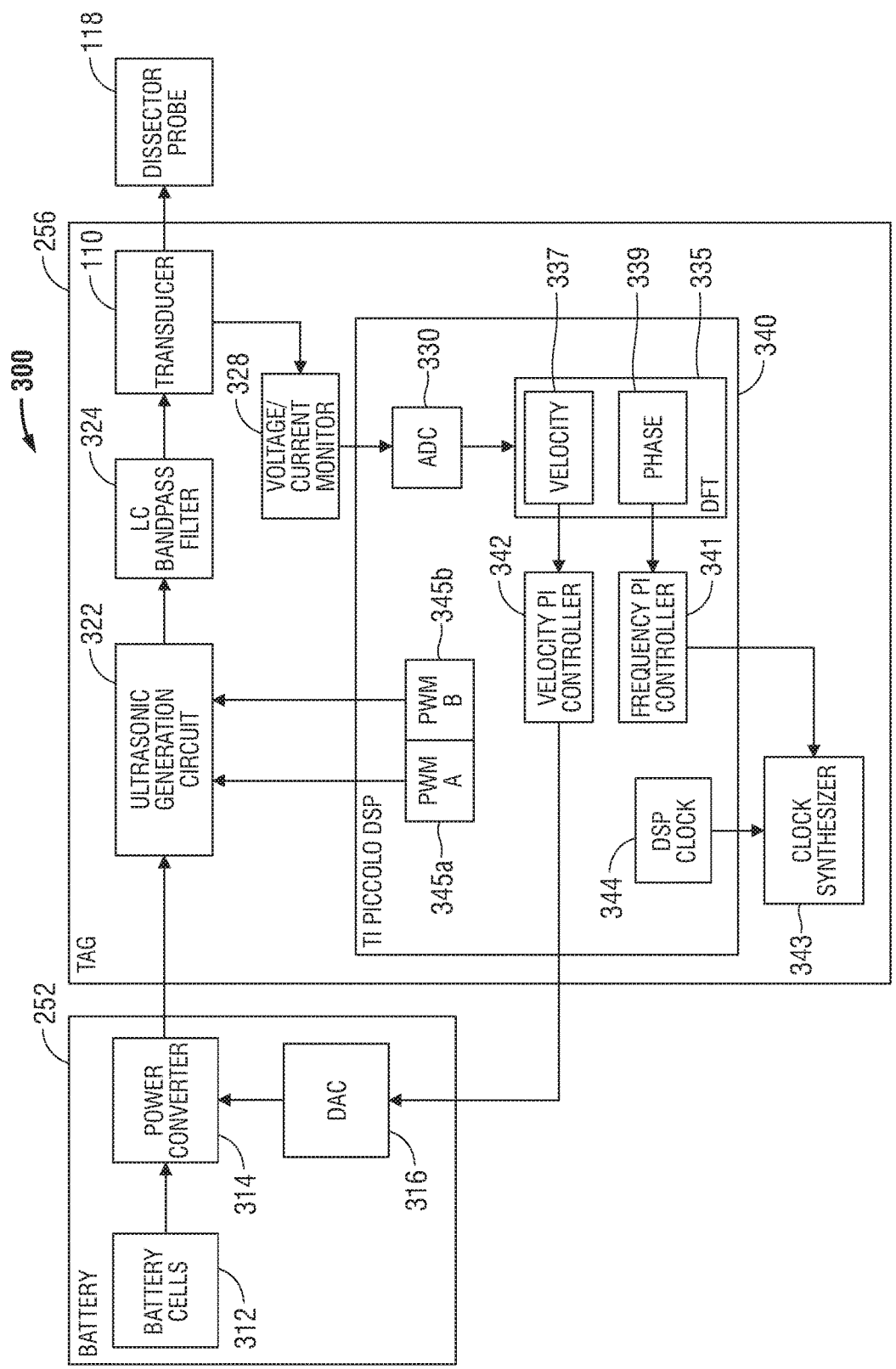
FIG. 3 is a block diagram of an ultrasonic surgical system, in accordance with one illustrative embodiment of the present disclosure.

As illustrated, for example, in FIG. 3, integrated transducer and generator (TAG) 256 includes both ultrasonic generation circuit 322 and transducer 110 (which are illustrated in FIG. 3) Like battery 252, TAG 256 may be removably connected to ultrasonic surgical instrument 250. Thus, in some embodiments, battery 252 and TAG 256 are reusable and the remainder of ultrasonic surgical device 250, including cannula 120, waveguide 114, and end effector 117, is disposable. As illustrated in FIG. 3, ultrasonic generation circuit 322 of TAG 256 takes direct current ("DC") from battery 252, converts it to alternating current ("AC"), and controls the AC to drive transducer 110 of TAG 256 to generate acoustic waves, which are propagated through waveguide 114 formed within cannula 120 to dissector probe 118, as described in greater detail below with reference to FIG. 3.

In some embodiments, end effector 117 is operated by an actuator mechanism 254. Pulling actuator mechanism 254 towards battery 252 (i.e., proximally) causes end effector 117 to close, for example, to clamp tissue in end effector 117. After clamping tissue in end effector 117, a user presses trigger 258 to cause power to be delivered from battery 252 to TAG 256 to cause transducer 110 to vibrate. TAG 256 transfers the acoustic waves generated by transducer 110 to waveguide 114, along which the acoustic waves propagate to dissector probe 118, causing dissector probe 118 to vibrate near or at the resonant frequency of transducer 110 in order to cut, seal, or coagulate tissue clamped by end effector 117. Transducer 110 of TAG 256 in combination with waveguide 114 and dissector probe 118 together form an oscillating structure.

FIG. 3 is a block diagram of ultrasonic surgical system 300 according to some embodiments of the present disclosure. In embodiments, ultrasonic surgical system 300 is configured for a cordless ultrasonic surgical device, such as ultrasonic surgical device 250 shown in FIG. 2. A similar system may be employed in corded ultrasonic surgical devices, as illustrated in FIG. 1. The components of ultrasonic surgical system 300 relate to aspects of digital motional current control as described herein.

As shown in FIG. 3, ultrasonic surgical system 300 includes battery 252, TAG 256, and dissector probe 118. Battery 252 includes battery cells 312, power converter 314, and digital-to-analog converter ("DAC") 316. TAG 256 includes ultrasonic generation circuit 322, band-pass filter ("BPF") 324 (such as an LC BPF), transducer 110, and transducer voltage and current ("TVC") measurement circuit 328, digital signal processor ("DSP") 340, and clock synthesizer 343. DSP 340, in turn, includes analog-to-digital converter 330 ("ADC"), Discrete Fourier Transform ("DFT") module 335, velocity proportional-integral ("PI") controller 342, frequency PI controller 341, digital signal processing ("DSP") clock 344, pulse width modulation ("PWM") circuit or module A 345a, and PWM circuit or module B 345b.

As an alternative to relying on electrical mains 106, as depicted in FIG. 1, the embodiment shown in FIG. 2 employs power derived from battery 252 containing battery cells 312 (or a group of batteries) small enough to fit either within the hand-piece or within a small box that attaches to an article worn by the user, for example, a waistband.

In the embodiment of FIG. 3, the output of battery 252 is fed to and powers TAG 256. Battery cells 312 output power to power converter 314, which may include a transformer or switching circuitry, which steps up the low voltage signals from battery cells 312 to a higher voltage. In one embodiment of the present disclosure, power converter 314 is configured as a boost converter to step up the voltage from battery cells 312 to a high voltage, such as 120V RMS. Transformers and switching circuitry are known in the art and are therefore not explained here in detail.

Ultrasonic generation circuit 322 includes switching circuitry (not shown), which generates an ultrasonic drive signal based on the power signal output by power converter 314 and the PWM signals output from PWM module A 345a and PWM module B 345b. Specifically, PWM module A 345a and PWM module B 345b provide PWM signals to the switching circuit, which switches the power provided by power converter 314 to generate an AC drive signal that is ultimately delivered to transducer 110. In some embodiments, prior to outputting the drive signal from ultrasonic generation circuit 322 to transducer 110, the drive signal is passed through LC BPF 324, which conditions the drive signal output from ultrasonic generation circuit 322 so that the drive signal is a smooth sinusoidal wave. The drive signal causes mechanical motion of transducer 110, which is transferred to dissector probe 118.

The configuration of LC BPF 324 may be dependent on DSP 340 and, more specifically, ultrasonic generation circuit 322. For example, where ultrasonic generation circuit 322 is a linear amplifier, LC BPF 324 may not be necessary because the output from ultrasonic generation circuit 322 is proportional to the sinusoidal input. Alternatively, if ultrasonic generation circuit 322 is a quasi-resonant converter, LC BPF 324 may be configured as a wide-band BPF. And, as another alternative, if ultrasonic generation circuit 322 produces a square wave, LC BPF 324 may be configured as a narrow-band BPF.

The systems and methods according to the present disclosure utilize DSP 340 in TAG 256 to ensure that the movement of waveguide 114 remains at or near resonance along waveguide 114 by maintaining the phase of the motional current ($i_M$) approximately equal to zero.

Resonance of dissector probe 118 is achieved when the motional current ($i_M$) of the transducer 110 and the voltage of the drive signal received by transducer 110 are in phase. To achieve this, TAG 256 uses TVC measurement circuit 328 to sense the motional current ($i_M$) and the voltage of the drive signal. ADC 330 samples the motional current and the voltage of the drive signal and DFT 335 determines the phase between the motional current and the drive signal and the magnitude or velocity of the drive signal. Frequency PI controller 341, clock synthesizer 343, DSP clock 344, PWM A module 345a, and PWM B module 345b operate together based on the determined phase to match a phase of the drive signal with a phase of the motional current $i_M$. The concept and technique of measuring motional current will be explained in detail below.

The motional current ($i_M$) measured by TVC measurement circuit 328 is fed back to DSP 340. DSP 340 calculates the phase of the motional current measured by TVC measurement circuit 328, and adjusts the frequency of the drive signal based on the phase of the motional current to achieve and maintain resonance of the ultrasonic transducer 110. Specifically, TVC measurement circuit 328 transfers the measured motional current and drive signal voltage, which are analog signals, to ADC 330, which converts the analog signals to discrete finite sequences of values. ADC 330 samples the measured motional current and drive signal voltage, and DFT module 335 performs a Discrete Fourier Transform on the sampled motional current and drive signal voltage to obtain phase information 339 of the sampled motional current with reference to the drive signal, and amplitude or velocity information 337 of the sampled drive signal voltage.

Velocity PI controller 342 uses velocity information 337 from DFT module 335 to alter the amplitude of the voltage signal output from DAC 316, thereby increasing or decreasing the amplitude of the drive signal transferred to transducer 110. DFT module 335 also controls frequency PI controller 341. Frequency PI controller 341 changes the frequency of the clock signal generated by the clock synthesizer 343 based on phase information 339. The clock synthesizer 343 then provides the clock signal to the DSP clock 344 of the DSP 340. PWM module A 345a and PWM module B 345b generate PMW signals, e.g., square waves, based on the frequency of DSP clock 344. Thus, by altering the frequency of DSP clock 344, the on-time and off-time of the PWM signals generated by the PWM module A 345a and PWM module B 345b may be altered. The PWM signals generated by PWM module A 345a and PWM module B 345b are used to drive ultrasonic generation circuit 322, which includes a switching circuit. The switching circuit generates the transducer signal or drive signal based on power output from ultrasonic generator 102 and the PWM signals generated by DSP 340.

Figure 4A:
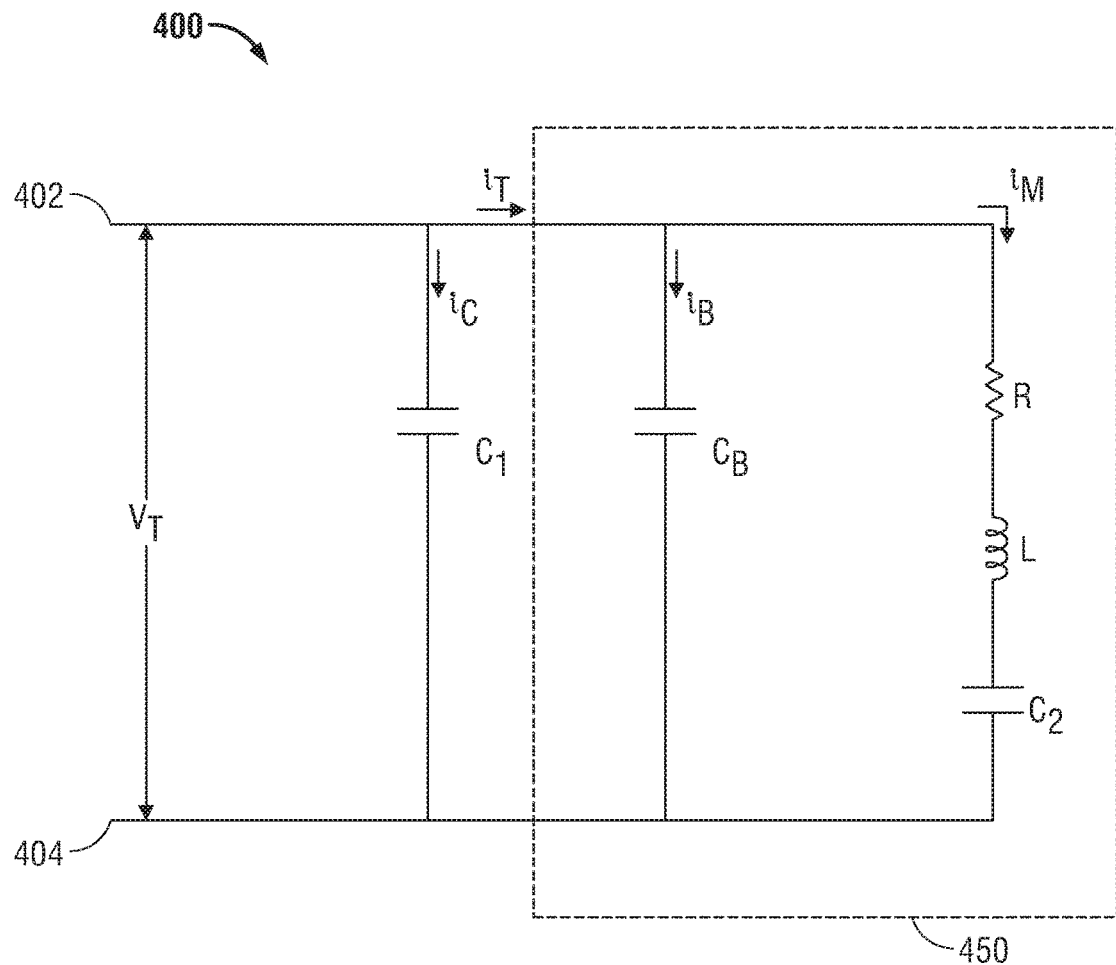
FIG. 4A is a circuit diagram of an ultrasonic transducer circuit, which includes an ultrasonic transducer model, for determining motional current.
Figure 4B:
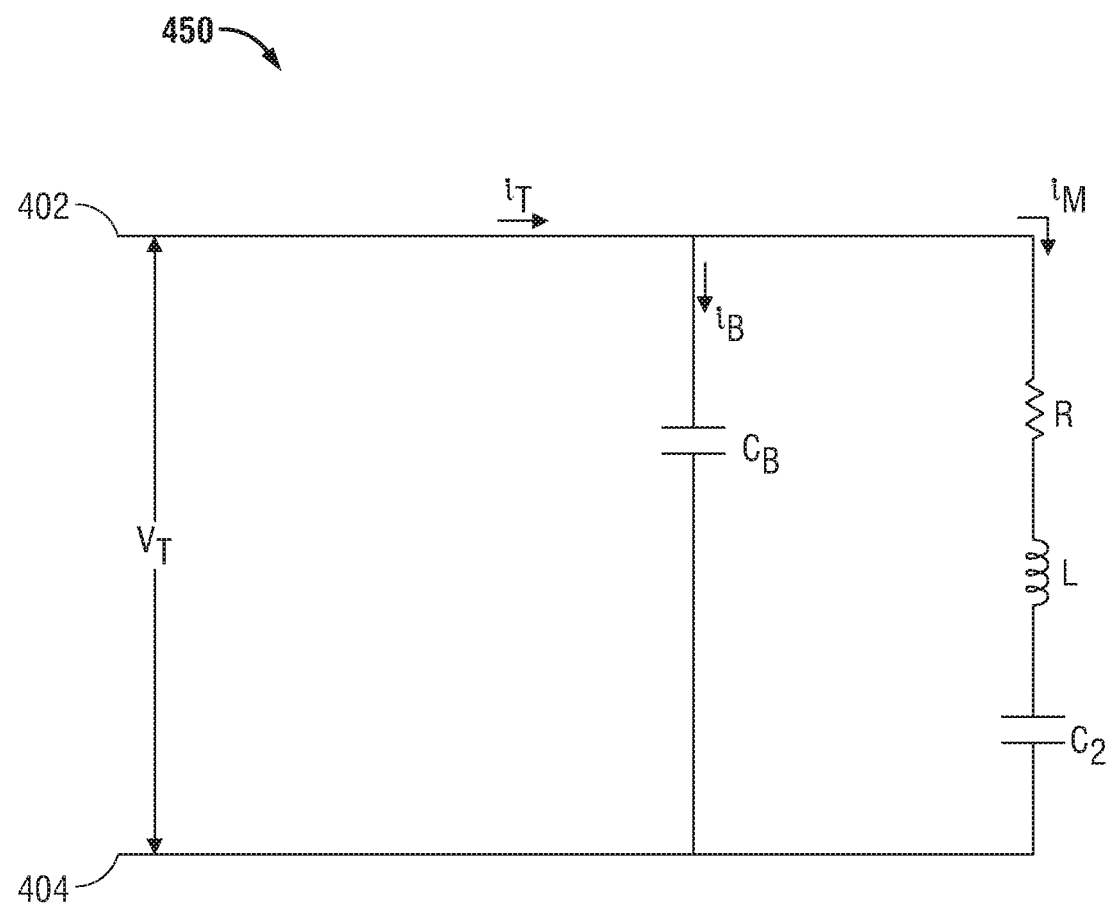
FIG. 4B is a circuit diagram of an ultrasonic transducer circuit, in accordance with illustrative embodiments of the present disclosure.

FIG. 4B is a schematic diagram of an electrical circuit representing a transducer model 450 of the mechanical properties of transducer 110. In embodiments, transducer 110 contains a stack of piezoelectric elements. The mechanical resonant frequency of the piezoelectric stack is a function of the mass and stiffness of the piezoelectric material used in the elements of the piezoelectric stack. Due to the piezoelectric effect, these mechanical properties manifest themselves as electrically equivalent properties. Thus, the mechanical mass, stiffness, and damping of transducer 110 may be represented by the transducer model 450 having a capacitor $C_B$, which is referred to herein as the bulk capacitance, arranged in parallel with a series RLC circuit (which is referred to herein as the series R-L-$C_2$ circuit) having a resistor R, an inductor L, and a capacitor $C_2$.

Flowing into input 402 of transducer model 450 is transducer current $i_T$. A portion of transducer current $i_T$ flows across the bulk capacitor $C_B$, which for the majority of the expected frequency range, retains a substantially static capacitive value. The remainder of transducer current $i_T$, i.e., the difference between transducer current $i_T$ and bulk capacitor current $i_B$, is defined as motional current $i_M$, which is converted into mechanical motion. Thus, motional current $i_M$ is the current that actually performs the work to move waveguide 114.

Some ultrasonic control systems regulate transducer current $i_T$. These systems, however, may not account for the bulk capacitor current $i_B$; thus, transducer current $i_T$ is not necessarily an indicator of the actual amount of current causing the mechanical motion of transducer 110 and waveguide 114. For instance, when dissector probe 118 moves from soft tissue to more dense material, such as bone, the resistance R increases greatly. This increase in resistance R causes less current $i_M$ to flow through the series R-L-$C_2$ circuit, and causes more current $i_B$ to flow across bulk capacitor $C_B$. As a result, an ultrasonic control system may not be able to cause the transducer 110 to resonate at the resonance frequency of the transducer, thus leading to suboptimal operation of the waveguide 114

To more precisely control the motional current $i_M$ in order to cause the transducer 110 to resonate at its resonant frequency, a capacitive element $C_1$ may be placed in parallel with transducer model 450 shown in circuit 400 of FIG. 4A. The value of capacitive element $C_1$ is selected so that $C_B/C_1$ is equal to a given ratio r. For efficiency, the chosen value for capacitive element $C_1$ is relatively low. This limits the current that is diverted from motional current $i_M$. When voltage $v_T$ is applied across terminals 402 and 404 of circuit 400, current $i_B$ flows across capacitive element $C_1$, transducer current $i_T$ flows into transducer 110, current $i_B$ flows across bulk capacitance $C_B$, and motional current $i_M$ flows across the series R-L-$C_2$ circuit. It follows that $i_M = i_T - r^* i_C$. This is because:

$$i_C = C_1 \cdot \frac{\partial V_T}{\partial_t} = \frac{C_B}{r} \cdot \frac{\partial V_T}{\partial_t} \text{ and } i_B = C_B \cdot \frac{\partial V_T}{\partial_t} \quad (1)$$

Therefore, $i_B = r^* i_C$ and, substituting for $i_C$ in the equation $i_M = i_T - i_B$, leads to $$i_M = i_T - r^* i_C. \quad (2)$$

By knowing transducer current $i_T$ and measuring current $i_1$ through capacitive element $C_1$, variations of the transducer's motional current $i_M$ can be monitored and regulated. The ultrasonic control system of the present disclosure eliminates the need for the capacitive element $C_1$. In some embodiments of the present disclosure, the bulk capacitance $C_B$ is estimated and the motional current $i_M$ is determined based on the estimated value of the bulk capacitance $C_B$, as described below. By determining the motional current $i_M$ in this way, an ultrasonic control system can cause the transducer 110 to resonate at or near the resonant frequency of the transducer 110 and thereby more precisely regulate the movement of waveguide 114.

In embodiments, to determine the resonant leg motional current $i_M$ from a sensed voltage $v_T$ and sensed current $i_T$ of a piezo resonant system with bulk capacitance $C_B$, one can use the following relationship between the bulk capacitance $C_B$ and the voltage $v_T$:

$$i_M = i_T - C_B \cdot \frac{d}{dt} v_T$$

The derivative of the sensed voltage $v_T$ may be computed by: (1) using a simple two-point difference method and then filtering the result using a low pass filter, (2) using a three-point central difference method without further filtering, or (3) using a three-point central difference method and then filtering the result using low pass filter for the best high-frequency rejection. In any case the goal is to do some computation with filtering, but without adding significant time-delay or phase distortion, thus allowing the computation to be done for self-resonant implementations based on the motional current.

In embodiments, one may simply low-pass filter data while preserving phase information with a single tap of sample delay by implementing an integer Hann moving average filter given by the following difference equation:

$$v\_filt_n := \frac{1}{4}(v_n + 2v_{n1} + v_{n2}).$$

The values n1 and n2 represent delay taps of one and two samples, respectively, of the input time-series sample sequence. The C psuedo-code to implement this is:

$$v\_filtn = (vn + vn1 << 1 + vn2) >> 2.$$

The two-point difference method may be given by the following difference equation:

$$dv_n := 1/T_S(v\_filt_n - v\_filt_{n1}).$$

This amounts to the difference between two consecutive samples of x in the time-series of input samples scaled by the sample frequency or one over the period between samples.

The derivative may alternatively be computed using the three-point central difference method, which may or may not include some low pass filtering. The difference equation may be given by:

$$dv_n := \frac{1}{2}T_S(v_n - v_{n2}).$$

The bulk capacitance $C_B$ of the ultrasonic surgical instrument can be measured at calibration time and thereafter the bulk capacitance $C_B$ can be updated according to the example methods described herein. Alternatively, the bulk capacitance $C_B$ could be measured periodically or continuously by the TAG 256 using a variety of methods.

Figure 5:
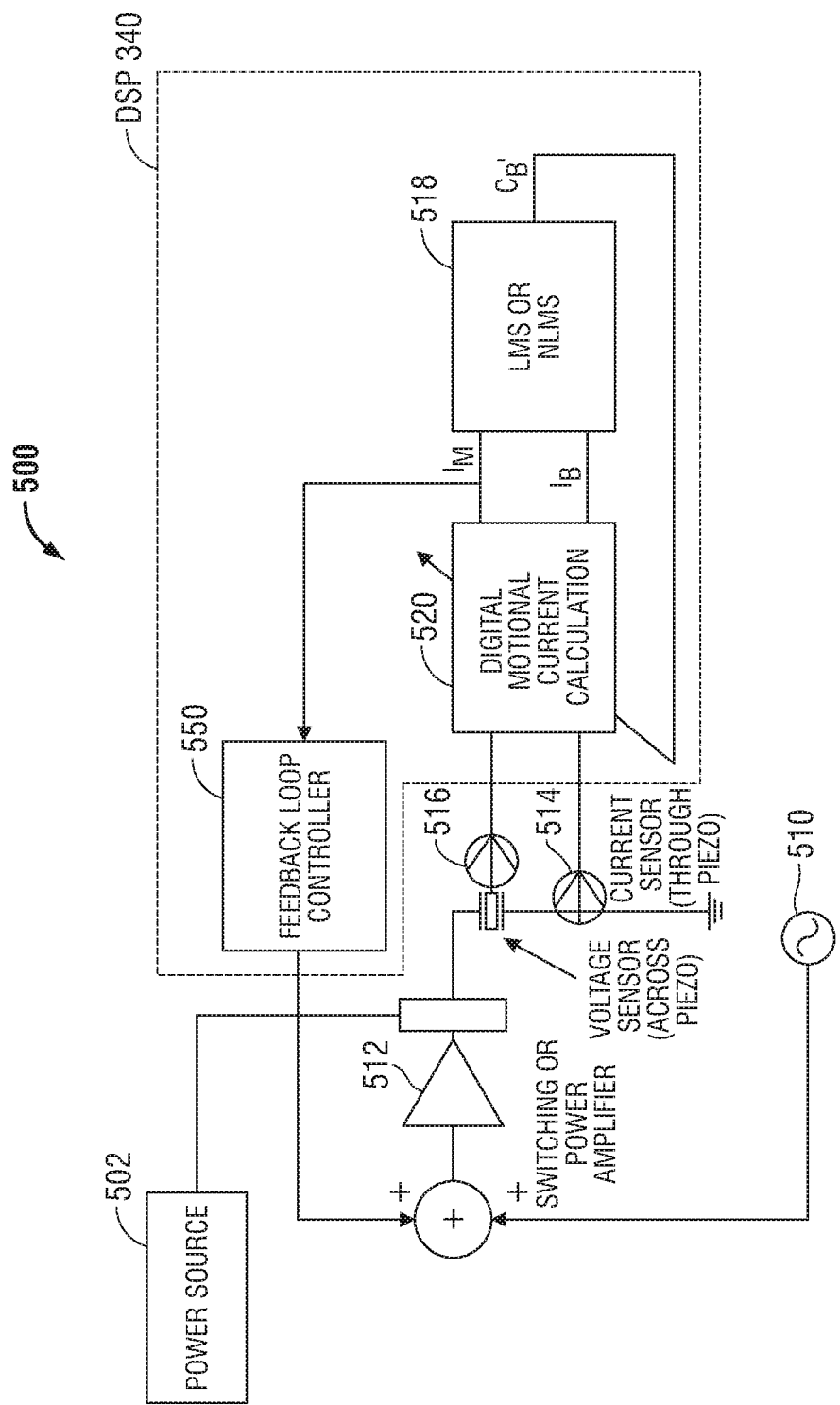
FIG. 5 is a block diagram illustrating a system for controlling an ultrasonic surgical instrument, in accordance with one illustrative embodiment of the present disclosure.

Referring now to FIG. 5, a block diagram of control circuit 500 for digital motional current control is illustrated. Included within control circuit 500 are power source 502, white noise generator 510, and switching or power amplifier 512. The power source 502 may be electrical mains 206 (e.g., according to the embodiment of FIG. 1) or battery 252 (e.g., according to the cordless embodiment of FIG. 2). Further included in control circuit 500 is DSP 340, which includes current sensor 514, voltage sensor 516, adaptive filter module 518 (which is shown in greater detail in FIG. 7), digital motional current calculation ("DMCC") module 520 (which is shown in greater detail in FIG. 6), and feedback loop controller 550. Switching or power amplifier 512 may be included in ultrasonic generation circuit 322 (e.g., according to the embodiment of FIG. 3) and both current sensor 514 and voltage sensor 516 may be included in TVC measurement circuit 328 (e.g., according to the embodiment of FIG. 3).

As shown in FIG. 5, white noise generator 510 is utilized to determine an initial value of bulk capacitance $C_B$ for transducer 110 and may be included within power source 502. It is contemplated that white noise generator 510 generates an input signal which is fed through circuit 450 and then the initial value of bulk capacitance $C_B$ is determined. In some embodiments, the determination of the initial value of bulk capacitance $C_B$ is completed during calibration of ultrasonic surgical instrument 250. The initial value of bulk capacitance $C_B$ may be determined at the time of manufacture as the nominal value. As shown in FIG. 5, ultrasonic generator 102 provides power to switching or power amplifier 512. The output of power amplifier 512 is sampled by voltage sensor 516 and current sensor 514 to determine the voltage applied across transducer 110 and the current flowing through transducer 110, respectively. As is shown in FIG. 3, voltage sensor 516 and current sensor 514 may be located in TVC measurement circuit 328.

The output of switch or power amplifier 512 is fed to DMCC module 520 which, in turn, outputs motional current $i_M$ and current $i_B$ to adaptive filter module 518. Adaptive filter module 518 is an adaptive filter utilizing, in embodiments, a least means square algorithm (LMS) or normalized LMS algorithm to determine and update values of bulk capacitance value $C_B$. Adaptive filter module 518, as described in further detail below with reference to FIG. 7, determines an updated value of bulk capacitance $C_B$ based on motional current $i_M$. The updated value of bulk capacitance $C_B$ is then fed back to DMCC module 520. Feedback loop controller 550 also receives motional current $i_M$, and, in some embodiments, is implemented as a phase-locked loop, which maintains resonance of transducer 110.

Figure 6:
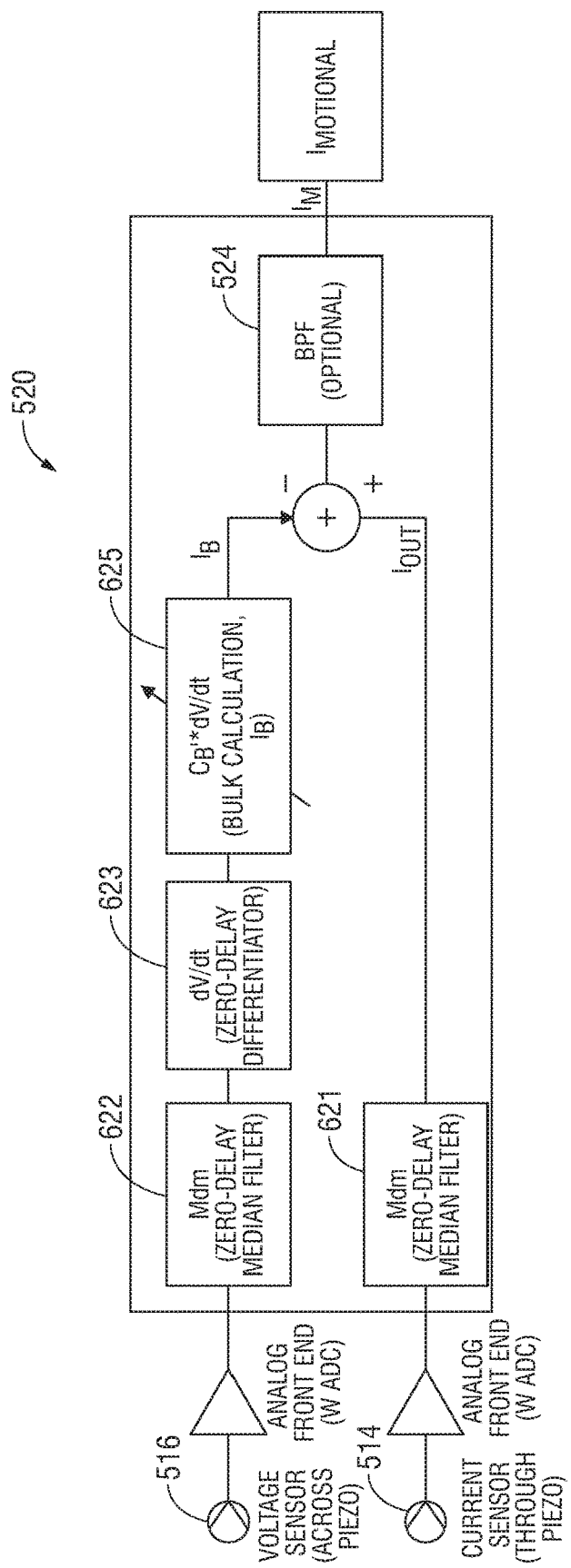
FIG. 6 is a circuit block diagram illustrating a digital motional current calculation module of FIG. 5, in accordance with one illustrative embodiment of the present disclosure.

FIG. 6 is a schematic circuit diagram of DMCC module 520. Included within DMCC module 520 are zero-delay median filters 621, 622, zero-delay differentiator 623, current calculator module 625, and LC band-pass filter (BPF) 324. Voltage sensor 516 and current sensor 514 provide the measured voltage across transducer 110 and the measured current through transducer 110, respectively, to DMCC module 520. The measured voltage across transducer 110 is passed through zero-delay median filter 622, which removes noise from the measured voltage. Zero-delay median filter 622 may be a Hann moving average filter. Once filtered, the measured voltage is passed though zero-delay differentiator 623, which determines the rate of change of the measured voltage (dV/dt). The rate of change of the measured voltage across transducer 110 is utilized by current calculator module 625 to determine the current $i_B$ through bulk capacitance $C_B$. Zero-delay differentiator 623 may use a two-point difference algorithm or a three-point difference algorithm to determine the rate of change of the measured voltage across transducer 110.

The measured current passing through transducer 110 is passed through zero-delay median filter 621, which removes noise from the measured current, and generates transducer current $i_T$. Once filtered, current $i_B$ through bulk capacitance $C_B$ is subtracted from current $i_T$ resulting in motional current $i_M$ as described above with reference to FIG. 4A. LC BPF 324 is optionally used to attenuate specific frequencies of the motional current $i_M$.

In another embodiment, the motional current $i_M$ may be determined by using the average or real power $P_{avg}$ and apparent power $P_{rms}$ based on the root mean square (rms) values of the current and voltage output from ultrasonic generator 102. For transducer 110, the average power $P_{avg}$ at resonance is equal to the apparent power $P_{rms}$. By sampling n samples of voltage V across transducer 110 and current I through transducer 110, the correlation coefficient xr between the time-series sample sequences $v_n$ and $i_n$ of length N is given by:

$$xr := \frac{\sum_{n=0}^{N-1}(v_n i_n)}{\sqrt{\sum_{n=0}^{N-1} v_n^2}\sqrt{\sum_{n=0}^{N-1} i_n^2}} \quad (3)$$

which is equal to the ratio of the real power to the apparent power or:

$$xr = \frac{P_{avg}}{P_{rms}} \quad (4)$$

The motional current $i_M$ at or near resonance is the current in the real leg or the RLC portion of transducer model 450. The motional current $i_M$ may be determined by scaling the rms current by the correlation coefficient xr as follows:

$$i_m := xr\sqrt{\frac{1}{N}\sum_{n=0}^{N-1} i_n^2}$$

Figure 7:
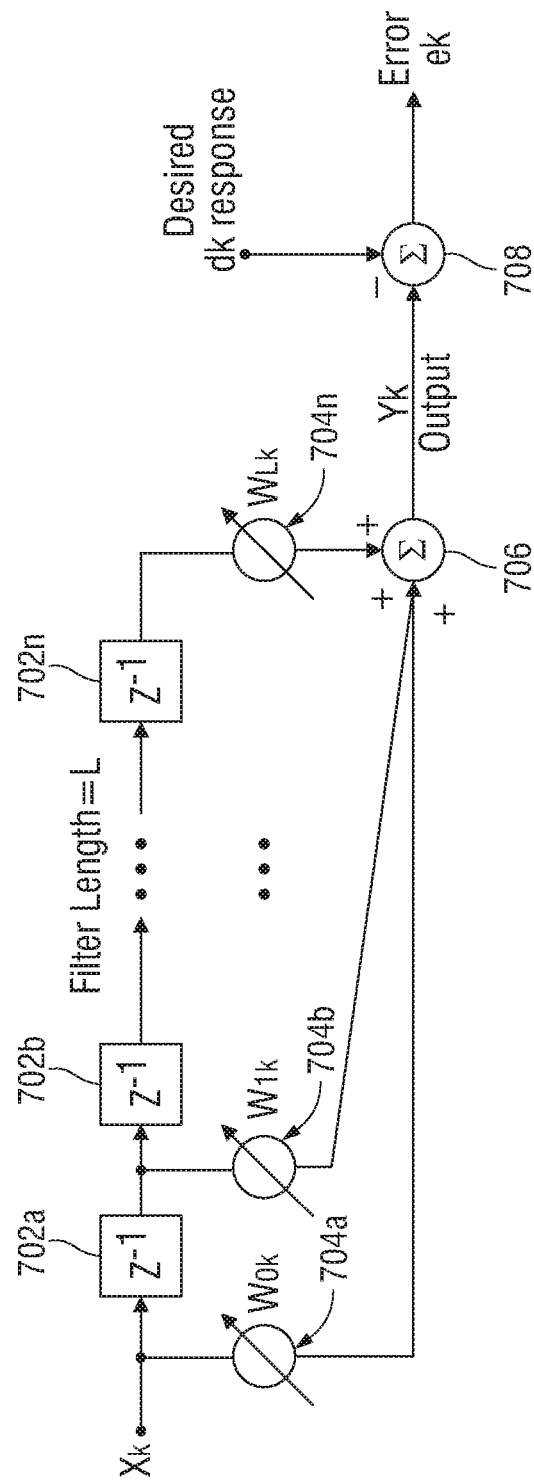
FIG. 7 is a system block diagram illustrating a least means squared filter of FIG. 5, in accordance with one illustrative embodiment of the present disclosure.

Referring now to FIG. 7, adaptive filter module 518 is described in greater detail. As shown in FIG. 7, adaptive filter module 518 is illustrated as an LMS filter. The LMS filter, which may be a finite impulse response ("FIR") filter, includes a series of time delay units 702a-702n and a series of weighting units 704a-704n coupled to an input signal $x_k$, which is the motional current $i_M$. During operation, first weighting unit 704a multiplies input signal $x_k$ by first weight value $w_{0k}$ of weight vector $\overline{w}_{k+1}$. Weight vector $\overline{w}_{k+1}$ is the updated bulk capacitance $C_B{}'$. The time delay units 702b-702n shift input signal $x_k$, and corresponding weighting units 704b-704n multiply the delayed input signal $x_k$ by corresponding weight values $w_{lk}, \ldots, w_{Lk}$ of weight vector $\overline{w}_{k+1}$. The results of time delaying and weighting input signal $x_k$ are added together by adder 706 to obtain output signal $y_k$.

The output signal $y_k$, which is a weighted value of the motional current $i_{Mk}$, is subtracted from the desired response signal $d_k$, which is the transducer current $i_T$, by subtractor 708 to obtain error signal $e_k$, which is the bulk capacitance current $i_{Bk}$. Thus, the LMS update equation to compute the weight vector or bulk capacitance update is given by:

$$C_B{}' = \overline{w}_{k+1} = \overline{w}_k + 2*\mu*i_{Mk}*i_{Bk}, \quad (5)$$

where μ is chosen by the designer and is bounded as follows:

$$0 < \mu < \frac{1}{\lambda_{max}} \quad (6)$$

where $\lambda_{max}$ is the greatest eigenvalue of the autocorrelation matrix of the motional current $i_{Mk}$.

Adaptive filter module 518 may also be configured to use a normalized least mean squares filter ("NLMS"). An NLMS filter is schematically configured similar to LMS filter of FIG. 7; however, the computation used to determine the value of bulk capacitance $C_B$ differs from the equations 3-5 above. For example, motional current $i_{Mk}$ and the bulk capacitance current $i_{Bk}$ may be used in the following NLMS update equation to compute the weight vector or bulk capacitance updates:

$$C'_B = \overline{w_{k+1}} = \overline{w_k} + \frac{1}{i_{Bk}^T * i_{Bk}} * i_{Mk} * i_{Bk}, \quad (7)$$

In the embodiments described herein, the data collected, the calculations made, and other parameters relating to the ultrasonic surgical instrument 250 may be stored locally within memory 352, which may be an EEPROM or other data storage device housed, for example, within TAG 256. This data may also be downloadable from memory 352 such that it can be later analyzed in the event a concern is raised regarding the use of the TAG 256 or other elements of ultrasonic surgical instrument 250.

Further, although several of the embodiments herein were described specifically with reference to the ultrasonic surgical instrument 250 depicted in FIG. 2, these concepts and control features are equally usable in other ultrasonic surgical systems including, but not limited to, those shown in FIGS. 1 and 2 and described in detail as ultrasonic surgical instrument 250 herein.

Figure 8:
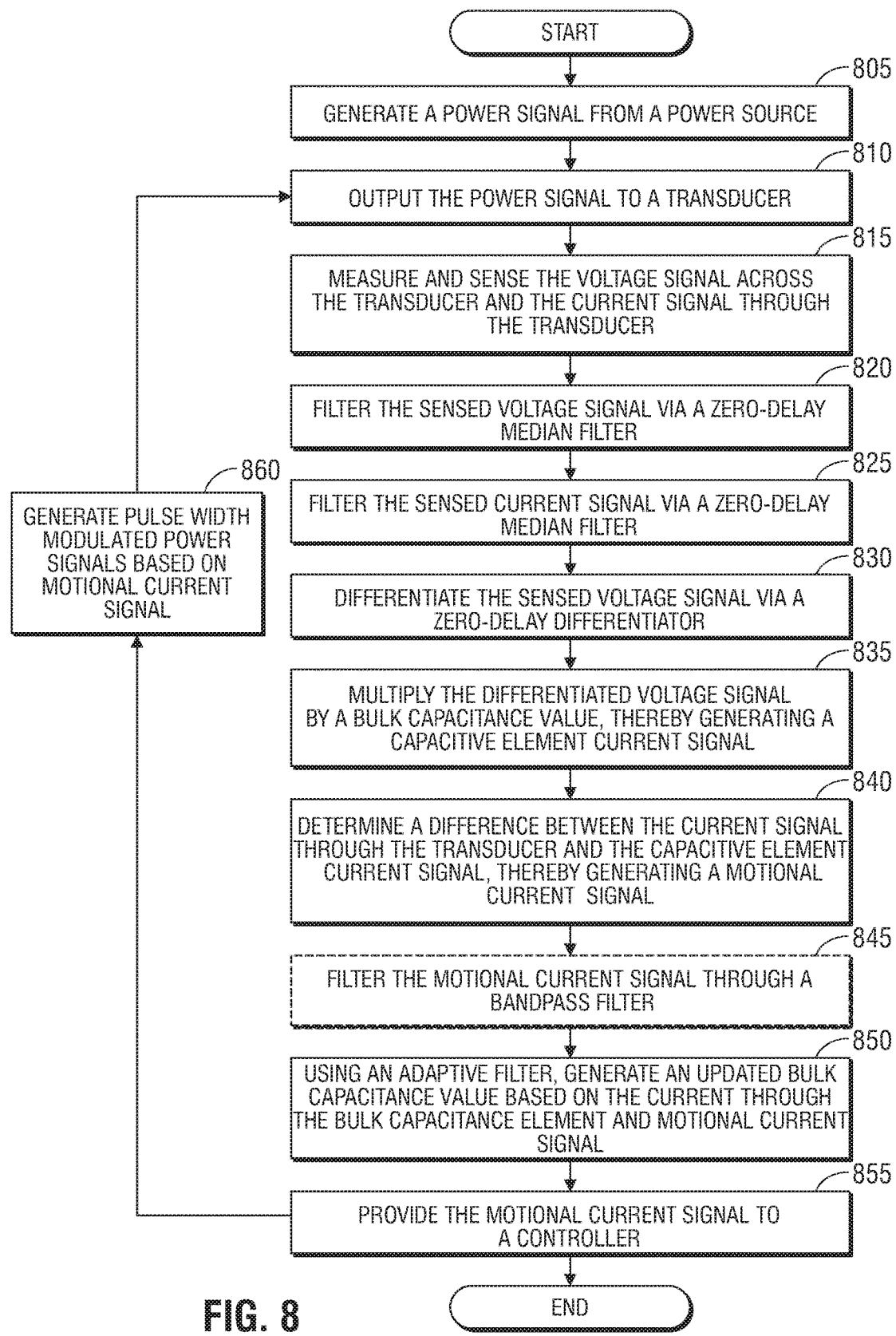
FIG. 8 is a flow diagram of a method for digital motional control of an ultrasonic surgical instrument, in accordance with one illustrative embodiment of the present disclosure.

FIG. 8 is a flowchart illustrating an example method 800 for digital motional current control for ultrasonic devices in accordance with the present disclosure. Method 800 may be implemented, at least in part, by processor 321 executing instructions stored in memory 352 (FIG. 3). The steps of method 800 may be executed in sequences other than the sequence shown in FIG. 8 without departing from the scope of the present disclosure. Furthermore, some steps shown in method 800 of FIG. 8 may be concurrently executed with respect to one another instead of sequentially executed with respect to one another.

At step 805, a power signal is generated from a power source, such as battery 252 (FIG. 2A). Next, at step 810, the power signal is output to a transducer, such as transducer 110, via an ultrasonic drive signal generation circuit. At step 815, the voltage signal across transducer 110 and the current signal through transducer 110 are sensed by TVC measurement circuit 328. As used herein, sensing the voltage signal and the current signal includes measuring and/or sampling the voltage and current signals. For example, voltage sensor 516 may measure and periodically sample the voltage signal across transducer 110 while current sensor 514 may measure and periodically sample the current signal through transducer 110.

Next, at step 820, the voltage signal sensed across transducer 110 is filtered by a zero-delay median filter, such as zero-delay median filter 622, which removes noise from the measured voltage signal. Next, at step 825, the sensed current signal is also filtered via a zero-delay median filter, such as zero-delay median filter 621. At step 830, the sensed and filtered voltage signal is differentiated, for example, by zero-delay differentiator 623. Next, at step 835, the differentiated voltage signal is multiplied by a bulk capacitance value $C_B$, as shown in equation (1), to determine current $i_B$ through bulk capacitance value $C_B$.

Next, at step 840, the difference between the sensed current signal $i_T$, which is filtered by the zero-delay median filter, and the bulk capacitance current signal $i_B$ is determined. This difference, as described above with reference to FIG. 4B, is motional current signal $i_M$, as shown in equation (2). Optionally, at step 845, motional current signal $i_M$ may be passed through a band-pass filter.

Next, optionally at step 850, using an adaptive filter, such as a least mean squares filter or a normalized least means squares filter, an updated bulk capacitance value $C_B'$ is generated based on motional current signal $i_M$ and current $i_B$ through bulk capacitance $C_B$, in accordance with equations (5) and/or (8) herein. The updated bulk capacitance value $C_B'$ is then used to determine motional current signal $i_M'$, which, in turn, is used as feedback to maintain resonance of transducer 110, as described herein.

Next, at step 855, motional current signal $i_M$ is fed back to a controller, e.g., frequency PI controller 341. At step 860, PWM modules 345a, 345b generate PWM signals, which are used to operate ultrasonic generator 102. Then, method 800 returns to step 810, where ultrasonic generator 102 generates and outputs a transducer signal to drive the transducer 110. It is contemplated that method 800 repeats steps 810-860 to adjust the transducer signal based on the updated bulk capacitance value $C_B'$ thereby digitally controlling the motional current of transducer 110 to maintain transducer 110 vibrating at or near resonance within ultrasonic surgical instrument 250.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in any appropriately detailed structure. Although specific embodiments of the present disclosure have been disclosed, those having ordinary skill in the art will understand that changes may be made to the specific embodiments without departing from the spirit and scope of the disclosure. The scope of the disclosure is not to be restricted, therefore, to the specific embodiments, and it is intended that the appended claims cover any and all such applications, modifications, and embodiments within the scope of the present disclosure.

From the foregoing, and with reference to the various figure drawings, those skilled in the art will appreciate that certain modifications may also be made to the present disclosure without departing from the scope of the same. While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling a transducer and generator assembly, comprising:
   sensing a current signal and a voltage signal at a transducer having a bulk capacitance, wherein the bulk capacitance has an initial bulk capacitance value;
   differentiating the voltage signal;
   multiplying the differentiated voltage signal by the initial bulk capacitance value to determine a bulk capacitance current signal;
   determining a difference between the current signal and the bulk capacitance current signal to determine a motional current signal corresponding to mechanical motion of the transducer;
   determining an updated bulk capacitance value for the bulk capacitance of the transducer based on the determined motional current signal and the bulk capacitance current signal;
   generating a transducer signal based on the motional current signal;
   driving the transducer with the transducer signal; and
   maintaining resonance of the transducer based on the updated bulk capacitance value using a phase locked loop.

2. The method of claim 1, further comprising:
   determining the initial bulk capacitance value prior to providing the transducer signal to the transducer.

3. The method of claim 2, further comprising:
   generating a test signal;
   transmitting the test signal to the transducer;
   sensing a response; and
   determining the initial bulk capacitance value based on the sensed response.

4. The method of claim 1, further comprising:
   determining the updated bulk capacitance value using a least mean squares adaptive filter.

5. The method of claim 1, further comprising:
   determining the updated bulk capacitance value using a normalized least mean squares adaptive filter.

6. The method of claim 1, further comprising:
   filtering the voltage signal using a zero-delay median filter; and
   differentiating the filtered voltage signal using a zero-delay differentiator.

7. The method of claim 6, further comprising sampling the voltage signal to obtain voltage data,
   wherein differentiating the voltage signal includes determining a rate of change of the filtered voltage signal.

8. The method of claim 7, wherein filtering the voltage signal, sampling the voltage signal, and determining the rate of change of the voltage signal are performed so that the results of filtering, sampling, and determining the rate of change are free of a time-delay or phase distortion greater than a pre-determined threshold.

9. The method of claim 7, further comprising:
   differentiating the voltage data using a two-point difference method; and
   filtering the differentiated voltage data using a low-pass filter.

10. The method of claim 9, wherein the low-pass filter is a Hann moving average filter.

11. The method of claim 7, further comprising differentiating the voltage data using a three-point central difference method.

12. The method of claim 11, further comprising filtering the differentiated voltage data using a low-pass filter.

13. The method of claim 12, wherein the low-pass filter is a Hann moving average filter.

14. The method of claim 1, further comprising:
    determining a frequency of the transducer signal based at least in part on a phase of the motional current signal.

15. The method of claim 1, further comprising:
    determining a root mean square voltage of the voltage signal;
    determining a root mean square current of the current signal; and
    determining an average power and an apparent power based on the root mean square voltage and the root mean square current.

16. The method of claim 1, further comprising:
    filtering the difference between the current signal and the bulk capacitance current signal using a band-pass filter to obtain the motional current signal.

17. The method according to claim 1, further comprising:
    sensing a second current signal and a second voltage signal at the transducer;
    differentiating the second voltage signal to obtain a second differentiated voltage signal;
    multiplying the second differentiated voltage signal by the updated bulk capacitance value to determine a second bulk capacitance current signal;
    determining a difference between the second current signal and the second bulk capacitance current signal to determine a second motional current signal corresponding to mechanical motion of the transducer.

18. The method according to claim 17, further comprising determining a second updated bulk capacitance value for the bulk capacitance of the transducer based on the second determined motional current signal and the second bulk capacitance current signal.

19. A transducer and generator assembly, comprising:
    a current sensor for sensing a current signal at the transducer having a bulk capacitance, wherein the bulk capacitance has an initial bulk capacitance value;
    a voltage sensor for sensing a voltage signal at the transducer;
    an analog-to-digital converter ("ADC") coupled to the current sensor and the voltage sensor for sampling the current signal and the voltage signal to obtain current signal data and voltage signal data;
    a hardware processor configured to:
      differentiate the voltage signal data to obtain differentiated voltage signal data;
      multiply the differentiated voltage signal data by the initial bulk capacitance value to obtain bulk capacitance current signal data,
      determine a difference between the current signal data and the bulk capacitance current signal data to obtain motional current signal data corresponding to mechanical motion of the transducer, and
      determine an updated bulk capacitance value for the bulk capacitance of the transducer based on the motional current signal data and the bulk capacitance current signal data;
    a transducer signal generator circuit configured to generate a transducer signal based on the motional current signal data and provide the transducer signal to the transducer; and
    a phase locked loop configured to maintain resonance of the transducer based on the updated bulk capacitance value.

20. The transducer assembly according to claim 19, wherein the hardware processor is further configured to:
 filter the voltage signal using a zero-delay median filter; and
 differentiate the voltage signal using a zero-delay differentiator.

* * * * *